(12) United States Patent
Efron

(10) Patent No.: US 9,681,801 B1
(45) Date of Patent: Jun. 20, 2017

(54) EFRON STEREOPTER

(71) Applicant: Marvin Efron, West Columbia, SC (US)

(72) Inventor: Marvin Efron, West Columbia, SC (US)

( * ) Notice: Subject to any disclaimer, the term of this patent is extended or adjusted under 35 U.S.C. 154(b) by 0 days.

(21) Appl. No.: 15/402,193

(22) Filed: Jan. 9, 2017

(51) Int. Cl.
| | |
|---|---|
| *A61B 3/08* | (2006.01) |
| *A61B 3/02* | (2006.01) |
| *A61B 3/028* | (2006.01) |
| *A61B 3/032* | (2006.01) |
| *A61B 3/00* | (2006.01) |

(52) U.S. Cl.
CPC .............. *A61B 3/08* (2013.01); *A61B 3/0008* (2013.01); *A61B 3/0075* (2013.01); *A61B 3/0091* (2013.01); *A61B 3/032* (2013.01)

(58) Field of Classification Search
CPC .. A61B 3/08; A61B 3/032; A61B 3/02; A61B 3/066; A61B 3/00; A61B 3/0325; A61B 3/06; A61B 3/028; A61B 3/063; A61H 5/00; H04N 13/0422
USPC .................................. 351/201, 203, 240, 243
See application file for complete search history.

(56) References Cited

U.S. PATENT DOCUMENTS

| | | | |
|---|---|---|---|
| 2,033,634 A | 3/1936 | Higley | |
| 2,391,248 A | 12/1945 | Koch | |
| 2,482,374 A | 9/1949 | Ruschmeyer | |
| 2,620,210 A | 12/1952 | Wuster | |
| 3,011,394 A | 12/1961 | Sherman et al. | |
| 3,844,641 A | 10/1974 | Nowak | |
| 4,035,066 A | 7/1977 | Slomski | |
| 4,247,216 A | 1/1981 | Pansini | |
| 4,260,226 A | 4/1981 | Ghahramani | |
| 4,506,963 A | 3/1985 | Cooper | |
| 4,573,717 A | 3/1986 | Peacock | |
| H293 H | 6/1987 | Task et al. | |
| 4,844,607 A | 7/1989 | Andera et al. | |
| 4,871,195 A | 10/1989 | Parrish | |
| 4,888,670 A | 12/1989 | Sharrah | |
| 5,223,865 A | 6/1993 | Shirao et al. | |
| 5,235,361 A | 8/1993 | Super | |
| 5,357,293 A | 10/1994 | Uomori et al. | |
| 6,412,827 B1 | 7/2002 | Barclay et al. | |

(Continued)

OTHER PUBLICATIONS

Winterbottom, Marc, et al. Operational Based Vision Assessment Research: Depth Perception. No. AFRL-SA-WP-JA-2014-0030. School of Aerospace Medicine Kettering OH Occupational and Environmental Health Dept/Risk Analysis BR, 2014.*

(Continued)

*Primary Examiner* — Scott J Sugarman
*Assistant Examiner* — Henry Duong
(74) *Attorney, Agent, or Firm* — Memminger E. Wiggins

(57) ABSTRACT

The present disclosure describes a variety of stereopter devices for testing depth perception using a plurality of three dimensional test sets which lack rotational symmetry around a bisecting horizontal plane. By means of the present stereopter device the plurality of test sets are presented against a uniformly lit and standardized background in each of two orientations to a test subject by rotation of a handle affixed to a housing which carries the test sets on planes orthogonal to a plane perpendicular to the axis of rotation. Following presentation of test sets in one orientation, the device is inverted for presentation of the test sets in the other orientation.

20 Claims, 7 Drawing Sheets

(56) References Cited

U.S. PATENT DOCUMENTS

| | | | |
|---|---|---|---|
| 6,517,204 | B1 | 2/2003 | Ghahramani |
| 7,267,437 | B2 | 9/2007 | Watkins |
| 7,445,398 | B2 | 11/2008 | Stockler |
| 7,538,876 | B2 | 5/2009 | Hewitt et al. |
| 8,491,119 | B2 | 7/2013 | Reichow et al. |
| 2011/0304708 | A1 | 12/2011 | Ignatov |

OTHER PUBLICATIONS

Kalloniatis M, Luu C. "The Perception of Depth." May 1, 2005 [Updated Jun. 6, 2007]. In: Kolb H, Fernandez E, Nelson R, editors. Webvision: The Organization of the Retina and Visual System [Internet]. Salt Lake City (UT): University of Utah Health Sciences Center; 1995-. Available online via the following link: http://www.ncbi.nlm.nih.gov/books/NBK11512/pdf/Bookshelf_NBK11512.pdf.

Heron, Suzanne and Lages, Martin. "Screening and sampling in studies of binocular vision." Vision Research, vol. 62(1), pp. 228-234 (Jun. 2012): School of Psycology, University of Glasgow, Scotland, UK. Copyright 2012 Elsevier Ltd. Accessible on-line via the following link: http://www.sciencedirect.com/science/article/pii/S0042698912001277.

Coutant, Ben E., and Westheimer, Gerald. "Population distribution of stereoscopic ability." Neurobiology Division. Department of Molecular and Cell Biology, University of California Berkeley. Berkeley, CA 94720, USA, Ophthal, Physiol, Opt., 13(1):3-7 (1993). Copyright 1993 Butterworth-Heinemann for British College of Optometrists 0275-5408/93/010003-05.

Verhoeff, F.H., M.D. "Simple Quantitative Test for Acuity and Reliability of Binocular Stereopsis." Archives of Ophthalmology. Dec. 1942. vol. 28, pp. 1000-1014. Copyright 1942 American Medical Association. United States.

Helveston, Eugene M. "Stereopsis and Strabismus." In Strabismus and Amblyopia: Experimental Basis for Advances in Clinical Managment, (Wenner-Gren International Symposium Series, vol. 49), vol. 49, p. 359 Springer, 1988.

* cited by examiner

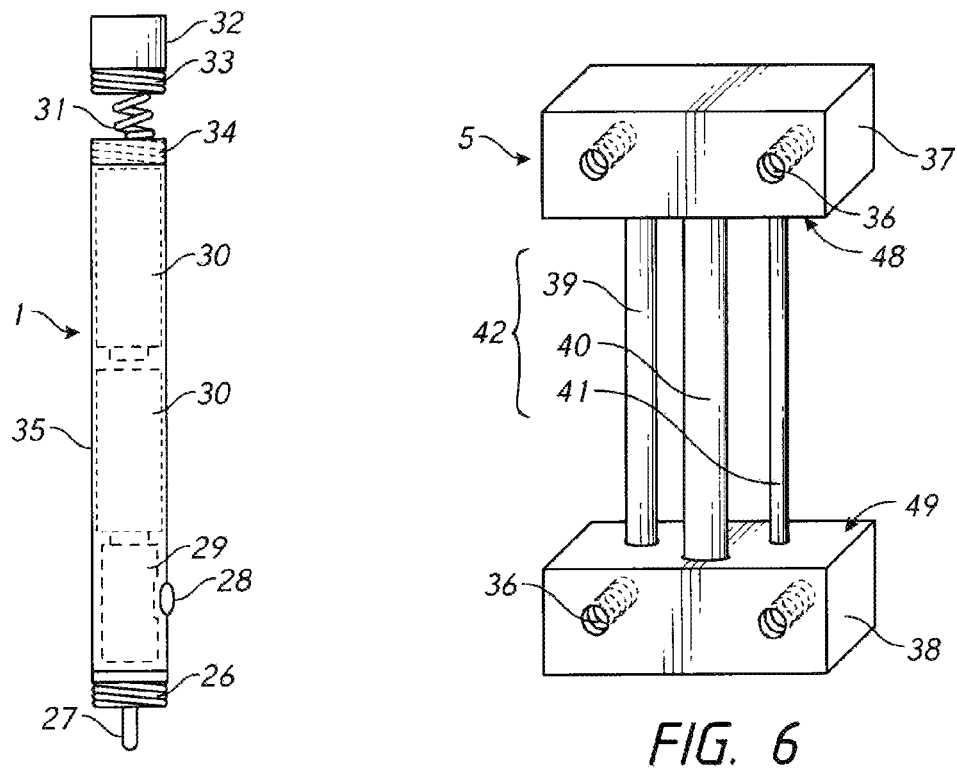
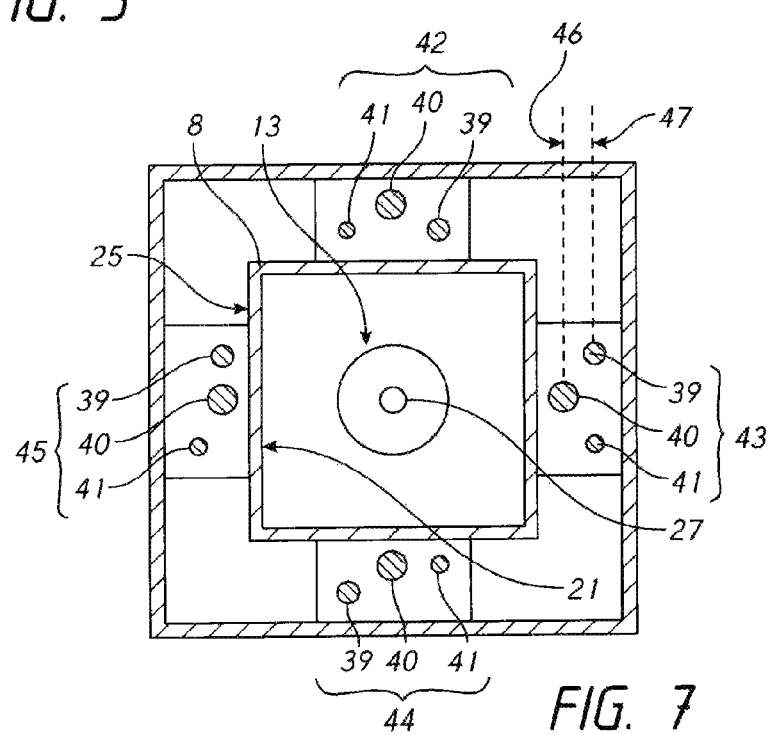
FIG. 5
FIG. 6
FIG. 7

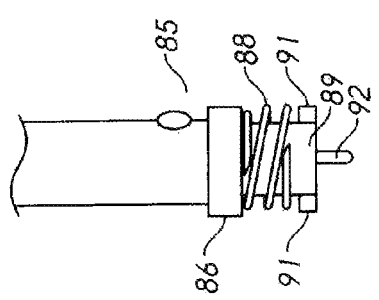
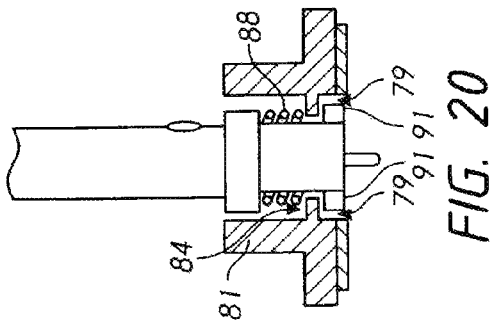
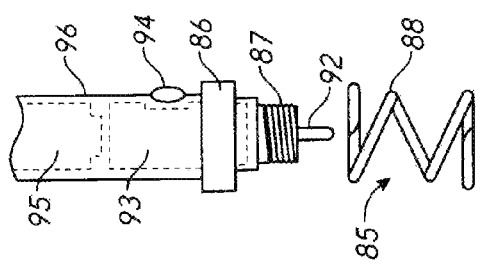
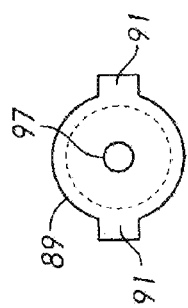
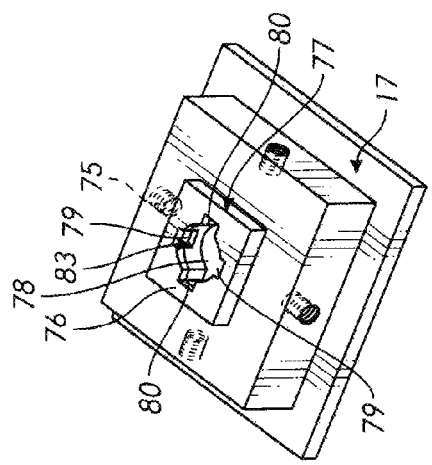
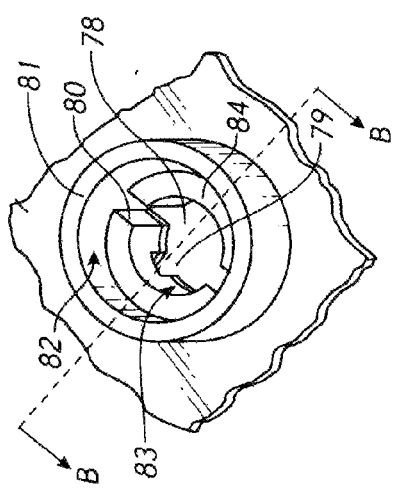

EFRON STEREOPTER

RELATED APPLICATIONS

Not Applicable.

STATEMENT AS TO RIGHTS TO INVENTIONS MADE UNDER FEDERALLY SPONSORED RESEARCH AND DEVELOPMENT

Not Applicable.

PARTIES TO A JOINT RESEARCH AGREEMENT

Not Applicable.

SEQUENCE LISTING

Not Applicable.

FIELD OF THE INVENTION

This invention relates to an apparatus for use in evaluating the level of depth perception in individuals. More specifically, this invention relates to an apparatus suitable for use in measuring the degree of depth perception in subjects.

BACKGROUND OF THE INVENTION

Stereopsis is the impression of depth that is perceived when a scene is viewed by someone with two eyes and normal binocular vision. Since the eyes of humans, and most animals, are located at different lateral positions on the head, binocular vision results in projection of slightly different images to the retinas of the eyes. The differences are mainly in the relative horizontal position of objects in the two images. These positional differences are referred to as horizontal disparities or, more generally, binocular disparities. Disparities are processed in the visual cortex of the brain to yield depth perception.

Stereopsis is not shared equally by all people. It has been found that people possess different degrees of stereo acuity, that is, different degrees to which objects may be perceived to lie in different planes when viewed binocularly. One study reports that 97% of test subjects were able to perceive depth differences at binocular disparities of 2.3 minutes of arc or smaller, and at least 80% of test subjects could perceive depth differences at a binocular disparity of 30 seconds of arc. See Coutant, B. E., et al., Ophthal. Physiol. Opt., 13(1):3-7 (1993). The inability to perceive depth of vision binocularly may be caused by conditions such as strabismus or for other less apparent reasons. Occupations requiring the precise judgment of distance sometimes include a requirement to demonstrate some level of stereopsis; in particular, this is the case for airplane pilots.

Monocular depth cues, which by definition are depth cues which only require use of one eye, include retinal image size, linear perspective, accommodation, and motion parallax.

Retinal image size permits depth judgments based on prior knowledge and familiarity with similar objects. If two objects are known to be of equal size and one appears larger than the other, than the smaller object is perceived to be further away. Similarly, if the size of an object is known, it is possible to estimate its distance by the size of its appearance.

When objects of known distance subtend a smaller and smaller angle, it is interpreted as being further away. This monocular cue, referred to as linear perspective, is commonly exemplified by the apparent convergence of train tracks as they recede into the distance.

Accomodation is an oculomotor cue for depth perception. When we try to focus on far away objects, the ciliary muscles stretch the eye lens, making it thinner, and hence changing the focal length. The kinesthetic sensations of the contracting and relaxing ciliary muscles (intraocular muscles) is sent to the visual cortex where it is used for interpreting distance/depth.

Motion parallax is created when an observer translates while viewing a rigid environment. While the observer's fixation is automatically maintained on a specific point, objects nearer or farther than the fixation point move relative to each other on the observer's retina. The visual system uses this relative movement of objects on the retina, motion parallax, as a cue to the relative depth of these objects in the environment.

Historically, laboratory stereopsis testing has been performed by measuring "real" depth perception utilizing special instrumentation. One of the oldest and best known of these "real" tests is the Howard-Dolman test. In the Howard-Dolman test the subject views two 1-cm diameter vertical rods at 6 meters through a horizontal aperture placed near the eyes that occludes the ends of the rods. The subject pulls a string attached to one rod until the two rods appear equidistant. Several monocular cues are present in this test, including the relative widths of the images of the rods and motion parallax due to head movements. Due to its large size, the Howard-Dolman device is impractical for use in clinical settings.

Another "real" test utilizes the Verhoeff Stereopter, described in Verhoeff, F H, Archives of Opthamology, 28:1000-1014 (1942). As described in the paper, the device comprises a rectangular black screen (target screen) at least 9 by 17.5 cm in size with its long axis vertical. In this is centered a rectangular window (target window) 1 by 5.4 cm in size, with its long axis horizontal. Immediately behind the window, held so that it can slide only vertically, is a smaller screen (sliding screen) 11 cm high, 6.9 cm wide and exactly 2.5 mm thick. The sliding screen contains four rectangular windows, each 16 by 50 mm in size, centered on the vertical midline with their long axes horizontal and separated from each other by distances of 5 mm. Crossing each window vertically are three thin black strips: one 3 mm in width centered exactly on the midline; one 2.5 mm in width centered 10.75 mm from the midline on one side of the 3 mm strip; and one 2 mm in width centered 10.50 mm from the midline on the other side. Of the strips, some are affixed to the back and the others to the front of the sliding screen, thereby providing a depth of 2.5 mm between the strips at the front and those at the back. By moving the sliding screen, any of the four sets of strips can be exposed in the target window, and by turning the device upside down, the positions of the lateral strips can be reversed. The sets are numbered from bottom upward. In set 1, the middle strip is at the front, the 2.5 mm strip at the back on the left and 2 mm strip at the front on the right. In set 2, the middle strip and 2.5 mm strips are at the back, and the 2.5 mm strip at the front on the left. In set 3, the middle and 2.0 mm strips are at the back, and the 2.5 mm strip is at the front on the left. In set 4, the middle strip is at the back, and the 2.5 and 2.0 mm strips (on the left and right) at the front.

Behind the target window of the Verhoeff Stereopter and about 3 mm behind the sliding screen is a stationary translucent diffusing screen 5.8 by 2 cm, which is indirectly attached to the target screen. During testing, the diffusing screen is evenly illuminated from behind, using for example, ordinary daylight from a window as a light source, or a 2.2 volt flashlight bulb and a curved reflector. Finally, Verhoeff further describes the stereopter as having a protective cover over the back of the device which is suitably marked so that each of the sets of strips can be identified from behind and, by the aid of a knob, placed in position by the examiner.

Verhoeff describes use of the stereopter for testing stereopsis as follows. During testing the device is kept centered as a frontal plane on the subject's binocular visual midline, and held steady to avoid monocular parallax. Verhoeff instructs that during testing, the target window should not be exposed while the device is being placed in position or the sets are changed. In particular, Verhoeff teaches that the examiner should grasp the device over the target window with the left hand, place the desired set into position with the right hand and then grasp the device below with the right hand and expose the target window by moving the left hand up or down.

Although the Verhoeff stercopter was commercialized, clinical practitioners considered testing using the device complicated, time consuming, requiring precise judgment and cooperation on the part of the test subject, and the device itself as cumbersome. Due to these constraints, the Verhoeff stereopter is not considered practical for use in a clinical setting. See, for example, HELVESTON, EUGENE M. "STEREOPSIS AND STRABISMUS." In Strabismus and Amblyopia: Experimental Basis for Advances in Clinical Management (Wenner-Gren International Symposium Series, Vol 49), vol. 49, p. 359. Springer, 1988. Consequently, the Verhoeff Stereopter has not been commercially produced for over fifty years.

The only "real" test currently used in clinical practice is the Frisby stereo plate test. The Frisby test uses transparent plates of varying thicknesses which are presented to the test subject one at a time against a clear background. Each plate is divided into four quadrants. The target of the test is a circular cluster of randomly arranged arrowheads of differing size printed on one side of each plate in one of the four quadrants. On the other side of the plate similar pattern elements are printed around the target and in the other three quadrants. For stereopsis screening, a test subject is asked to identify the target quadrant upon repeated trials wherein the position of the target quadrant is randomly selected. According to the manufacturer, an observer lacking normal binocular stereovision fails to detect the target as it can be distinguished only on the basis of binocular disparity cues to depth, as long as the plate is held stationary, viewed square-on, and placed about 5-10 cm in front of a clear background.

The Frisby stereo plate test suffers from a number of deficiencies. First, the plate must be held in a particular spatial relationship to a separate plain background provided on the box which holds the plates. This requirement necessitates that the box and plate be administered while resting on a table or on the lap of the examiner. Second, consecutive presentations of the same plate require the examiner to randomly turn the plate around unobtrusively, for example, while holding the plate behind their back. This adds considerably to the amount of time required to administer the test. Finally, no means are provided to ensure optimal lighting conditions for viewing the tests, and care must be taken to avoid reflections or shadows caused by light sources behind or over the patient. This limits the settings and conditions under which the test may be administered.

While "real" tests of depth perception rely on binocular disparities created when viewing a three dimensional scene with two eyes, binocular disparities can also be simulated by artificially presenting two different two dimensional images (referred to collectively as a stereogram) separately to each eye using a method called stereoscopy. Vision care practitioners have for the past century used devices for viewing stereograms to measure stereo acuity in patients. Stereograms produced for this purpose are sold commercially by several manufacturers. The most commonly used stereograms fall into two groups, namely those featuring contours which provide monocular cues as to the form or symbol in the stereograms, and those without such cues, which latter group is known as random dot stereograms. When viewing a stereogram of this nature through dissociating polarized lenses the patient with normal stereopsis perceives images of objects in the stereogram to be displaced either forwardly or rearwardly of the plane of regard or fixation being looked at. This illusion is achieved by creating on the stereogram a form having stereo disparity. The larger the degree of stereo disparity of the symbol being observed, the further it appears to be displaced relative to the plane of regard and hence the easier will it be for the patient to discriminate between the form and its reference ground. The ability to see the apparent displacement can hence be used as a measure of the patient's stereo acuity.

Some practitioners favor use of stereogram-based stereoscopic tests since by design such tests eliminate monocular (non-stereoscopic) depth cues typically present in "real tests," such as accommodation, motion parallax resulting from head movements, texture perspective, and/or the relative widths of stimuli based on size of the retinal image. Notwithstanding this perceived advantage, care must be taken with interpreting the results of stereogram-based tests since some people with otherwise normal stereoscopic vision have difficulty fusing random-dot stereograms, especially if they they cannot correctly focus on the stimulus.

Depth perception is an important skill needed in many facets of life, such as driving, flying, and in many occupations and leisure activities. In performing daily activities, depth perception is the result of stereoscopic vision, utilizing both eyes, and/or monocular vision skills.

SUMMARY OF THE INVENTION

The present disclosure describes a variety of stereopter devices for testing real depth perception using a plurality of three dimensional test sets which lack rotational symmetry around a bisecting horizontal plane. By means of the present stereopter device the plurality of test sets may be presented against a uniformly lit and standardized background in each of two orientations to a test subject by rotation of at least one handle affixed to a housing which carries the test sets on planes orthogonal to a plane perpendicular to the axis of rotation. Following presentation of test sets in one orientation, the device can be inverted for presentation of the test sets in the other orientation. Unlike many stereo instruments the present device does not use polarizing lenses to divide the images from the two eyes of a test subject to evaluate stereopsis. Such a technique works well when the subject being tested has equal vision in both eyes. However, a subject with only one eye, a subject with little vision in one eye, or a subject that suppresses vision in one eye will fail this type of stereoptic test even though the subject may actually have depth perception by using other visual clues learned by experience. Since the present stereopter does not use the polarizing lenses technique, it is therefore a valid instrument with all individuals, including those with only one eye to measure depth perception. Accordingly, the devices of the present invention permit rapid testing of "real" depth perception. A summary of selected aspects of such devices is provided below.

In a first aspect, a stereopter device comprises: a housing having a top, bottom and a lateral surface or surfaces; at least three real depth perception test sets coupled to the lateral surface or surfaces of the housing such that the planes defined by the vertical and horizontal axes of the test sets intersect to define the side surfaces of a right prism with a substantially convex regular polygonal base such that the positions of the test sets are rotationally symmetrical with one another relative to a central axis, and wherein each test set lacks rotational symmetry around a horizontal plane bisecting the test set; windows in the lateral surface or surfaces of the housing which are aligned with each test set so as to permit the test set to be viewed; a diffuser defining an interior space within the housing which is interior to the test sets, wherein the diffuser has planar faces rotationally symmetrical with one another relative to the central axis which are aligned with and substantially parallel to the test sets; at least one actuatable light source capable of illuminating the interior space defined by the diffuser, and at least one elongated handle attached to the top or bottom surface of the housing whereby the longitudinal axis of the handle is substantially aligned with the central axis, and whereby rotation of the handle permits test sets to be individually rotated into the field of vision of a stationary test subject.

Embodiments of the first aspect may include one or more of the following features. The number of lateral surfaces is identical to the number of test sets. The lateral surfaces are substantially planar and identical in number to the number of test sets, and wherein each lateral surface is substantially parallel to a plane defined by the vertical and horizontal axes of a single test set. The number of lateral surfaces is 3, 4, 5, 6, 7 or 8. The number of lateral surfaces is 4, 6 or 8. The number of test sets is 3, 4, 5, 6, 7 or 8. The number of test sets is 4, 6 or 8. The actuatable light source is a lamp electrically connected to a switch and at least one battery. The actuatable light source is a lamp on an end of a handle, wherein the lamp is electrically connected to a switch and at least one battery contained in the handle. The handle is a quick-release handle capable of removable attachment to the top and bottom surfaces of the housing.

A second aspect is a stereopter device of the first aspect, or an embodiment thereof, which comprises two handles, one attached to each of the top and bottom surfaces of the housing and substantially aligned with the central axis.

Embodiments of the second aspect may include one or more of the following features. Both handles comprise batteries and a switch electrically connected to a lamp at the proximal end of the handle. Both handles are capable of removable attachment to the housing. Both handles are quick-release handles.

A third aspect is a stereopter device of the first or second aspect, or an embodiment thereof, wherein the device further comprises an internal frame and the lateral surfaces of the housing are capable of facile coupling and decoupling to the internal frame by means of a quick-release connection.

Stereopter devices of the present invention will become apparent from the following detailed description considered in conjunction with the accompanying drawings in which like reference numerals designate identical or corresponding elements in each of the several views. It is to be understood, however, that the drawings are designed solely for purposes of illustration and not as a definition of the limits of the invention, for which reference should be made to the appended claims. One skilled in the art to which the invention pertains will recognize that numerous alterations and structural changes may be made to the embodiments disclosed in the drawings without departing from the principle, essence, or the spirit of the invention as described herein. It should be further understood that the drawings are not necessarily drawn to scale and that, unless otherwise indicated, they are merely intended to conceptually illustrate various stereopter device embodiments.

BRIEF DESCRIPTION OF THE DRAWINGS

Various stereopter device embodiments of the present invention are described herein with reference to the drawings wherein:

FIG. 5 is an elevation view of a quick-release handle for use with the stereopter device shown in FIG. 1;

FIG. 6 is a perspective view of an exemplary test set usable with the stereopter device shown in FIG. 1;

FIG. 7 is a cross-sectional view along line A-A of FIG. 4 showing an exemplary arrangement of test sets in the stereopter device shown in FIG. 1;

FIG. 15 is a perspective view of the interior side of an alternative end plate usable with the stereopter device embodiments shown in FIGS. 1 and 9 and adapted for use with an alternative quick-release handle design;

FIG. 16 is an enlarged perspective view of the exterior central portion of the end plate shown in FIG. 15;

FIG. 17 is an elevation view of the proximal end of an unassembled quick-release handle usable with the end plate shown in FIGS. 15-16;

FIG. 18 is a bottom elevation view of cap 89 shown in FIG. 17;

FIG. 19 is an elevation view of the proximal end of the assembled quick-release handle shown in FIG. 17; and FIG. 20 is a cross-sectional view along line B-B of the end plate shown in FIG. 16 following insertion and rotation of the proximal end of the assembled quick-release handle shown in FIG. 19.

DESCRIPTION OF PREFERRED EMBODIMENTS

Figure 1:
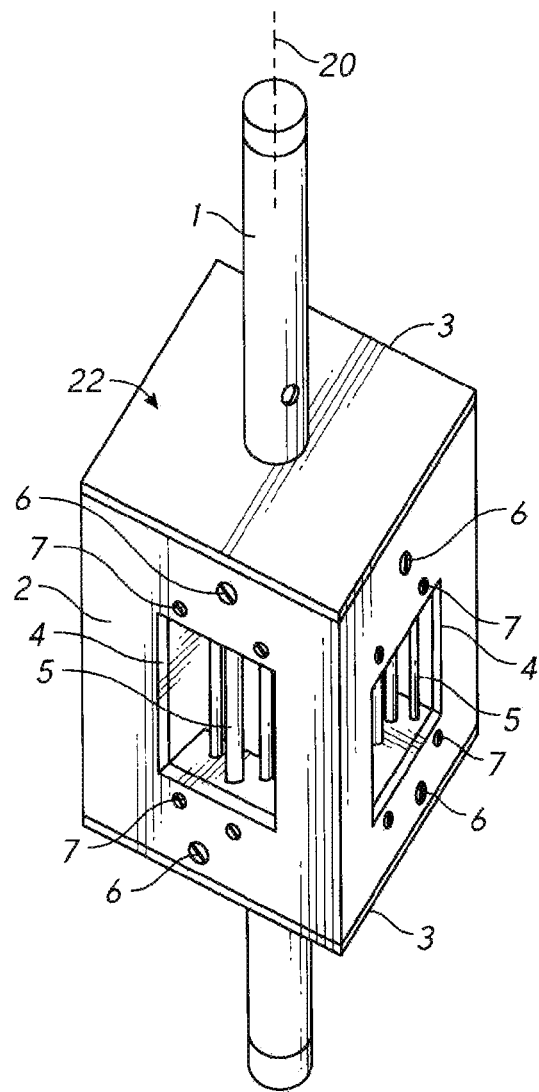
FIG. 1 is a perspective view of a fully assembled first stereopter device in accordance with the first and second aspects of the present disclosure.
Figure 2:
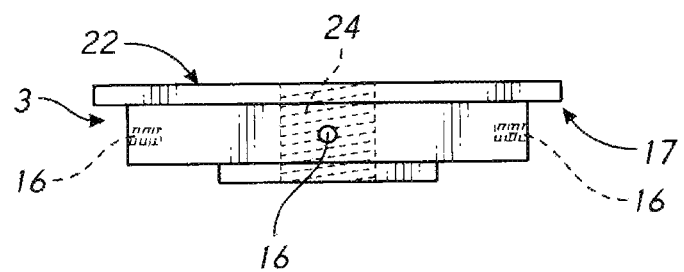
FIG. 2 is an elevation view of the upper end plate 3 shown in FIG. 1.
Figure 3:
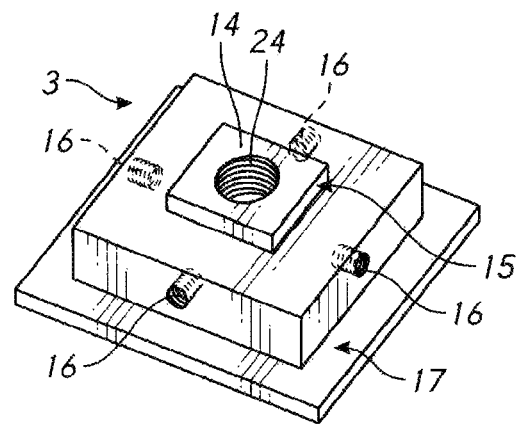
FIG. 3 is a perspective view of the interior side of the lower end plate 3 of the assembled stereopter device shown in FIG. 1.

Prior to referring to the drawings, definitions are offered to assist the reader in an understanding of this description.

A "real depth perception test set" utilizes at least two test objects arranged in three dimensional space to create binocular disparities between the at least two such test objects when viewed by a test subject capable of perceiving depth. Such "real" test sets by definition exclude use of a depth perception test set which is based on an artificial binocular disparity created from viewing of one or more two dimensional images.

A "convex regular polygon" is a polygon that is equiangular (all angles are equal in measure), equilateral (all sides have the same length), and all angles are less than 180 degrees.

A "prism" is a polyhedron having two surfaces that are polygons in parallel planes, while the other surfaces are parallelograms.

A "right prism" is a prism whose side surfaces are rectangular.

A "quick-release connection" is a connection between components that permits such components to be coupled or decoupled with no tools in a few seconds rather than the type of connection that requires tools, bolting and unbolting, and the like or otherwise a permanent installation. Quick release connections can be, for example, by snaps, magnets, Velcro, hand or coin tighten screws or fasteners, spring latches, latches actuatable by simple rotation, and the like.

A "quick-release handle" refers to a handle designed to be coupled or decoupled from the top and/or bottom surface of a stereopter device housing of the present disclosure with no tools in a few seconds rather than a type of connection that requires tools, bolting and unbolting, and the like or otherwise a permanent installation. Those of skill in the art will recognize that the design of the coupling elements on both the handle and top and/or bottom surface of the housing will depend on whether additional components of the stereopter device (for example, a lamp) are contained in the proximal end of the handle. Where this is the case, exemplary quick-release handles include the specific handle embodiments shown in the drawings, as well as any other type of connection mechanism known in the art adaptable for use in the device. Other well known types of mechanical connections which could be adapted for use in the device include: various plug and socket arrangements; lever actuated cam locks (see, for example, U.S. Pat. Nos. 4,871,195 and 6,412,827); lever actuated clamps (see, for example, U.S. Pat. Nos. 2,482,374 and 4,573,717); any of various frictional interference fits between two components, at least one of which has resiliently biased portions which engage portions of the other when pushed together, and, optionally, twisted. Quick-release mechanisms for handles which are hollow at the attachment point include in addition to the above, mechanisms involving use of spring pins or latches. Merely by way of example, reference is made to U.S. Pat. Nos. 2,620,210, 4,247,216, 7,445,398.

The term "substantially," e.g., in the expressions "substantially convex regular polygonal base," "substantially square," "substantially rectangular cuboid housing," "substantially centered," "substantially rectangular," "substantially aligned," "substantially concentric," "substantially parallel," "substantially identical," etc., means at least about 90% correspondence with the feature recited, e.g. Of course, at least 95% correspondence is more preferable, and as close to 100% correspondence with the feature recited as is practicable is most preferred. With respect to a "convex regular polygonal base," the relevant feature is the angle of the vertices. With respect to "square," the relevant feature is both angles and side dimensions. With respect to "rectangular" and "rectangular cuboid housing," the relevant features are both angles and dimensions of parallel edges.

The singular forms "a", "an" and "the" are intended to include the plural forms as well, unless the context clearly indicates otherwise. It will be further understood that the terms "having," "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the description of exemplary embodiments, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion.

In describing specific elements of stereopter devices of the present disclosure, when an element is referred to herein as being "connected" or "coupled" to another element, it can be directly connected or coupled to the other element or intervening elements may be present. In contrast, when an element is referred to herein as being "directly connected" or "directly coupled" to another element, there are no intervening elements present. Moreover, although the drawings illustrate connection of some elements by means of screws, any other fastening means such as a rivet, weld or other known fastening device may be used provided such means does not interfere with the operation or construction of the device.

A first stereopter device in accordance with the present disclosure is shown in FIGS. 1-7, where FIG. 1 illustrates the fully assembled device. The device includes a substantially rectangular cuboid housing defined by four lateral side walls 2, and substantially identical top and bottom end plates 3. Desirably, each of the lateral side walls 2 has substantially identical widths such that the housing is substantially square along its vertical axis. Substantially centered on each of the lateral side walls 2 is a substantially rectangular test window 4 for viewing a depth perception test set 5. Desirably, all test windows 4 have the same dimension. The corners of the windows 4 may be rounded if desired.

The two end plates 3 are coupled to the lateral side walls 2 using screws 6 inserted through bore holes 10 on the lateral side walls into threaded cavities 16 on the end plates. Alignment of the end plates 3 is facilitated by use of an overhanging flange 17 dimensioned so as to permit engagement and alignment with either the top edge 18 or bottom edge 19 of the lateral side walls 2.

Test sets 5 are coupled to the interior side 38 of the lateral side walls 2 using screws 7 inserted through bore holes 9 on the lateral side walls into threaded cavities 36 on the upper 37 and lower 38 structural members of each test set (see FIG. 6). It is important that the lower surface 48 of the upper structural member 37, and the upper surface 49 of the lower structural member 38, not be visible to the test subject during testing since this would clearly provide an obvious monocular cue as to the depth relationship of test objects attached to the structural members. Accordingly, the lower surface 48 of the upper structural member 37, and the upper surface 49 of the lower structural member 38, should at minimum align with the upper and lower edges of the test windows 4, but more preferably, respectively lie above and below these upper and lower edges of the test windows.

The device further comprises at least one handle 1, but more preferably two handles, one attached to each end plate 3 in a direction normal to the exterior surface 22 of the end plate by helically threaded, mating portions 24 on the end plates 3 (see FIGS. 2-3) and proximal ends 26 of the handle barrels 35 (see FIG. 5). When attached, the handles 1 are substantially aligned on a common central vertical axis 20 (see FIG. 1).

Figure 4:
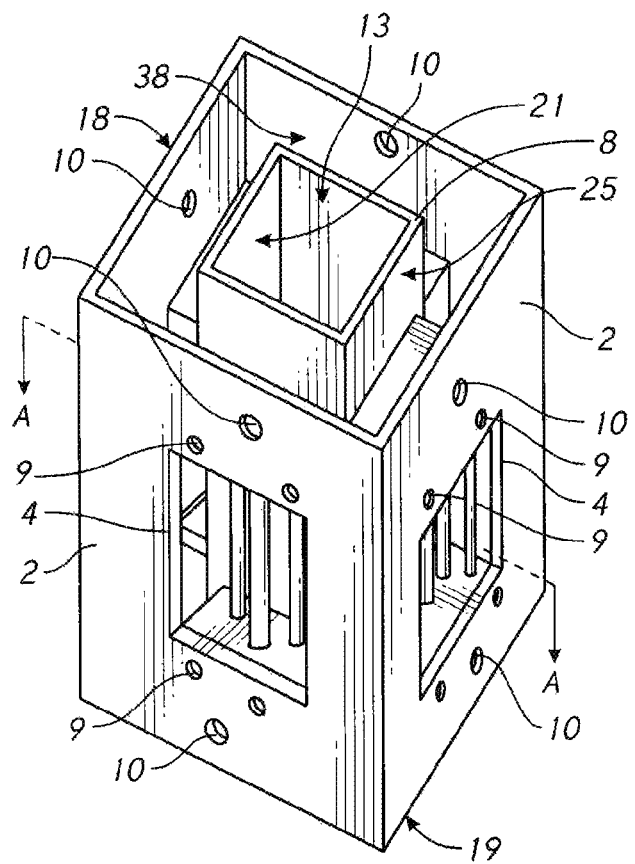
FIG. 4 is a perspective view of the interior of the stereopter device shown in FIG. 1 when both end plates 3 are removed.

Referring to FIG. 4, the first stereopter device in accordance with the present disclosure also comprises a substantially rectangular diffuser 8. The side walls of the diffuser are substantially concentric with the test sets 5 (see FIG. 1) and lateral side walls of the housing 2. During testing, a light source or sources are used to illuminate the internal space 13 defined by the interior surface 21 of the diffuser 8. The preferred light source or sources utilized for stereopters in accordance with the present disclosure is a lamp (or lamps) 27 (see FIG. 5) such as an incandescent light bulb or light-emitting diode (LED) positioned on the proximal end of one or both handles 1. The purpose of illuminating the internal space 13 of diffuser 8 is to provide a standardized and uniformly lit background for viewing test sets 5, as well as to eliminate the appearance of perceptible shadows which might otherwise be cast by test objects (39, 40, and 41 in FIG. 6) onto the outer surface 25 of diffuser 8 (see FIG. 4) as a result of ambient light sources external to the stereopter device during testing. Shadows from test objects could reveal the relative depth of test objects, and therefore this potential monocular depth cue is preferably minimized or eliminated for purposes of testing.

The diffuser 8 can be made of any material or materials used to diffuse light. A wide variety of such materials are well-known to those skilled in the art, and any such materials can be employed according to the present disclosure. To further facilitate uniform illumination of internal space 13, end plates 3 may further comprise a substantially rectangular reflecting element 14 having lateral surfaces 15 which are dimensioned so as to oppose the inner surface 21 of the diffuser 8 (see FIGS. 3-4). For a miniature LED lamp, a suitable material for both the diffuser 8 and the reflecting element 14 is ⅛ inch thick, translucent, white, plexiglass.

Referring to FIG. 5, at least one of the handles 1 comprises a tail cap 32 coupled to the distal end of barrel 35 by helically threaded, mating portions on the tail cap 33 and barrel 34. Accordingly, the tail cap 32 is removable to permit facile installation or removal of one or more batteries 30 from the barrel 35. The lamp 27 may be electrically connected through a simple single-pole switch 29 which is actuated by a switch button 28 to electrically connect and disconnect the lamp 27 to a DC voltage source, such as that provided by one or more batteries 30. A cap spring 31 may be employed to ensure good contact between the batteries and switch. All battery types, rechargeable and single use are contemplated. It is preferred, however, that the batteries be of the primary cell sizes commonly referred to in the industry as AA, and AAA batteries.

Where only one of the handles 1 is constructed to provide a light source, it is preferred that the other handle have a sufficiently identical exterior appearance such that a knowledgeable test subject (i.e., a test subject previously tested or otherwise familiar with the device) would not be able to determine the initial orientation of the test sets 5.

It will also be appreciated by skilled artisans that the battery or batteries, switch, and switch button, and other components used to create an electrical conductive path with the lamp or lamps used to illuminate the interior space defined by the diffuser need not be integral to one or both handles. Thus, alternative device embodiments wherein these components are incorporated into the housing, for example, in a space lying between an end plate and the diffuser, are within the scope of the present disclosure.

Test sets used in stereopter devices of the present invention utilize real objects positioned in three dimensional space and lack rotational symmetry around a horizontal plane bisecting the test sets. This characteristic doubles the number of visually distinct test sets capable of presentation to a test subject by simple inversion of the device. A preferred design for a test set lacking rotational symmetry utilizes at least two test objects (more preferably at least three test objects) of non-uniform size randomly affixed in each test set at any of two or more predefined depths. In addition to producing asymmetry, use of non-uniform size test objects is desirable in order to eliminate retinal image size as a cue to depth, thereby making binocular disparity the predominant cue for perceiving the differences in depth of the test objects.

Referring to FIGS. 6-7, a preferred design for test sets 5 consists of three vertical rods coupled between upper 37 and lower 38 structural members, and having diameters of 2.5 mm 39, 3.0 mm 40, and 2.0 mm 41. Depending on the test set (42, 43, 44, and 45 in FIG. 7), each of the three different width rods (39, 40, 41) are affixed in either a far 46 or in a near 47 position (as viewed through test windows 4—see FIG. 1). It is preferred that the 3.0 mm rod 40 be centered on the vertical midline of test window 4, the 2.5 mm rod 39 centered 10.25 mm from the vertical midline on one side of the 3.0 mm rod, and the 2.0 mm 41 rod centered 10.5 mm from the vertical midline on the other side of the 3.0 mm rod.

An arrangement of four exemplary test sets (42, 43, 44, and 45) is shown in FIG. 7. As viewed by a test subject, in a first set 42 the 3.0 mm rod 40 is in a center near position, the 2.5 mm rod 39 in a far left position, and the 2.0 mm rod 41 in a far right position. In a second set 43, the 3.0 mm rod 40 is in a center far position, the 2.5 mm rod 39 in a near right position, and the 2.0 mm rod 41 in a near left position. In a third set 44, the 3.0 mm rod 40 is in a center far position, the 2.5 mm rod 39 in a near left position, and the 2.0 mm rod 41 in a far right position. In a fourth set 45, the 3.0 mm rod 40 is in a center far position, the 2.5 mm rod 39 in a far left position, and the 2.0 mm rod 41 in a near right position.

Other sets could also be used in the device. First, a test set can be used having the 3.0 mm rod in a center near position, the 2.5 mm rod in a far right position, and the 2.0 mm rod in a near left position. Second, a test set can be used having the 3.0 mm rod in a center near position, the 2.5 mm rod in a near left position, and the 2.0 mm rod in a far right position. Finally, test sets may be constructed in which all three rods are affixed in either a near or far position. It is preferred, however, that all of the test sets have at least one rod in a near position and at least one rod in a far position.

Those skilled in the art appreciate that binocular disparity depends on the physical depth between two test objects, the interpupillary distance of the test subject, and the distance of a test subject from the nearest test object. For purposes of the present invention, a preferred observation distance is between 1-2 meters, most preferably 1 meter. For observation distances of 1 meter, a preferred range of depth distance between far 46 and near 47 positions for test objects is 2-3 mm, most preferably, 2.5 mm. Because the average interpupillary distance for adult females and males is 62 mm and 65 mm respectively, a 2.5 mm depth difference amounts to approximately 32 and 33.4 seconds of arc at an observation distance of 1 meter. For testing children, a preferred depth difference between far and near positions is 3 mm at an observation distance of 1 meter.

Figure 8:
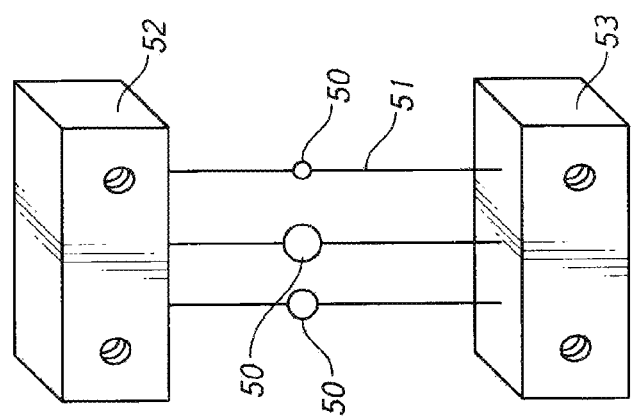
FIG. 8 is a perspective view of an alternative test set design.

Those skilled in the art will also recognize that other test sets can be designed suitable for use in the stereopter devices of the present disclosure. For example, with reference to FIG. 8, alternative test sets may be designed using variable sized beads 50 strung in either a near or far position between upper 52 and lower 53 structural members using thin wire or monofilament 51.

The dimensions of the stereopter device depicted in FIG. 1 and of its parts are unimportant within rather wide limits. A suitable height for the lateral side walls 2 is between about 8 cm and about 16 cm, more preferably between about 10 cm and about 14 cm, most preferably about 12 cm. A suitable width for the lateral side walls 2 is between about 6 cm and about 12 cm, more preferably between about 8 cm and about 10 cm, most preferably about 9 cm. A suitable height for test windows 4 is between about 2 cm to 9 cm, more preferably between about 3 cm to about 6 cm, most preferably about 4 cm. A suitable width for test windows 4 is between about 2 cm and about 8 cm, more preferably between about 3 cm and about 5 cm, most preferably about 3 cm. Regarding shape, the test windows 4 are preferably rectangular, but may be of any shape which permits binocular disparity produced by the objects in the test sets to be readily perceived by test subjects under the intended conditions of use.

The housing, handles, and test sets may be constructed from any suitable materials, but are preferably metal. Aside from the inner diffuser, all exterior surfaces, and any interior surfaces visible through test windows (including test objects), are preferably coated with a non-reflective dark material, for example, dull black paint. Moreover, there should be no obvious defects by which an astute test subject (i.e., a test subject familiar with the specific test sets used in the device) could detect whether the device as initially presented during testing has a specific orientation (that is, with one or the other handles up).

Regarding operation of the first stereopter device embodiment, during testing an examiner turns on at least one light source, or if necessary, multiple light sources by actuation of one or more single-pole switches 29. The examiner then grips at least one handle, more preferably both handles, and while holding the device in a vertical orientation, sequentially or randomly presents each test set 5 centered as a frontal plane on the test subject's binocular visual midline. In order to minimize monocular motion parallax it is important during presentation of a test set to hold the device steady, particularly with respect to any rotation about the central vertical axis 20 of the device. The subject should also be instructed to hold his/her head steady. Additional instructions will depend on the nature and design of the test sets. For test sets having the design illustrated in FIGS. 6-7, the test subject could be instructed: "There are three bars. One of the three is not in alignment with the other two. Which one is it and tell me if it is nearer or farther from the other two." Following each response by the test subject, the examiner rotates the device around the central vertical axis to present the next test set. Following presentation of each of the test sets, the examiner can invert the device 180 degrees and again sequentially or randomly present each test set 5 centered as a frontal plane on the test subject's binocular visual midline.

Any number of scoring methods may be used to assess depth perception by means of the first stereopter embodiment. The main criteria used to select a scoring method is that it provide the degree of discrimination desired. For example, where a rough estimate is desired, patients can be assigned a simple pass-fail score based on their ability to provide correct depth judgments of all test sets at a single preselected test distance. Alternatively, a test subject may be assigned as having a specific percentage of stereopsis at a single preselected test distance based on the percentage of correct judgments of all test sets. Finally, where a greater degree of reliability of the test subject's ability to perceive depth by stereopsis is desired, the test can first be performed while having the test subject cover their non-dominant eye. The ability of the test subject to perceive depth based on binocular disparities is indicated only if the percentage of correct responses using binocular vision exceeds the percentage of correct responses using monocular vision.

Figure 9:
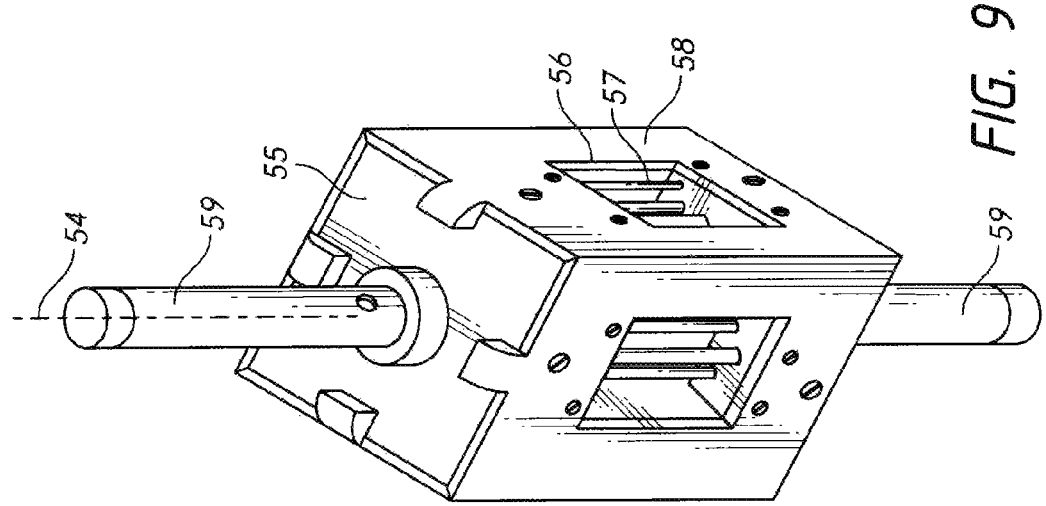
FIG. 9 is a perspective view of a fully assembled second steopter device in accordance with the third aspect of the present disclosure.

A second stereopter device embodiment in accordance with the present disclosure is shown in FIGS. 9-14, where FIG. 9 illustrates the fully assembled stereopter device. Like the first device embodiment, the second device embodiment includes a generally rectangular cuboid housing defined by four lateral side walls 58 having substantially identical widths such that the housing is substantially square along its vertical axis, substantially identical top and bottom end plates 55, and handles 59 substantially aligned on a common central vertical axis 54 and attached in a direction normal to the end plates 55. Also like the first device embodiment, each lateral side wall 58 has a substantially rectangular test window 56 for viewing a test set 57. Desirably, all test windows 56 have substantially the same dimensions. Finally, like the first device embodiment, the second device embodiment comprises a generally rectangular diffuser (not shown) and at least one light source (not shown) for illuminating the internal space defined by the lateral walls of the diffuser.

Figure 11:
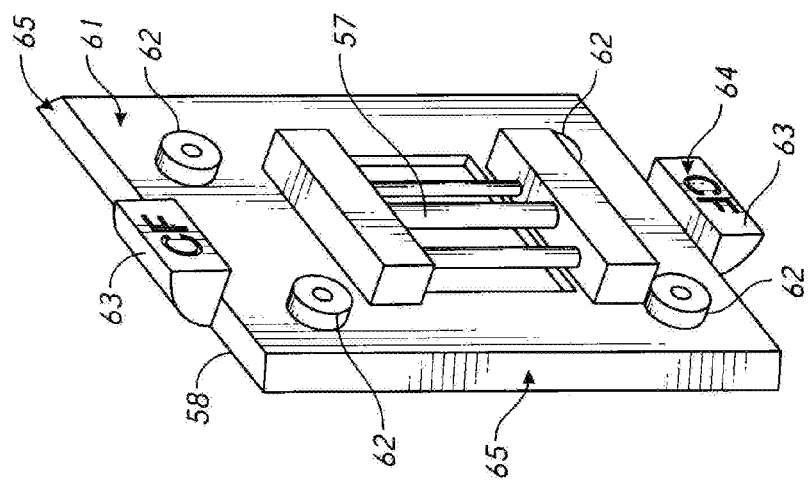
FIG. 11 is a perspective view of the interior side of a detachable lateral side wall of the stereopter device shown in FIG. 9.
Figure 10:
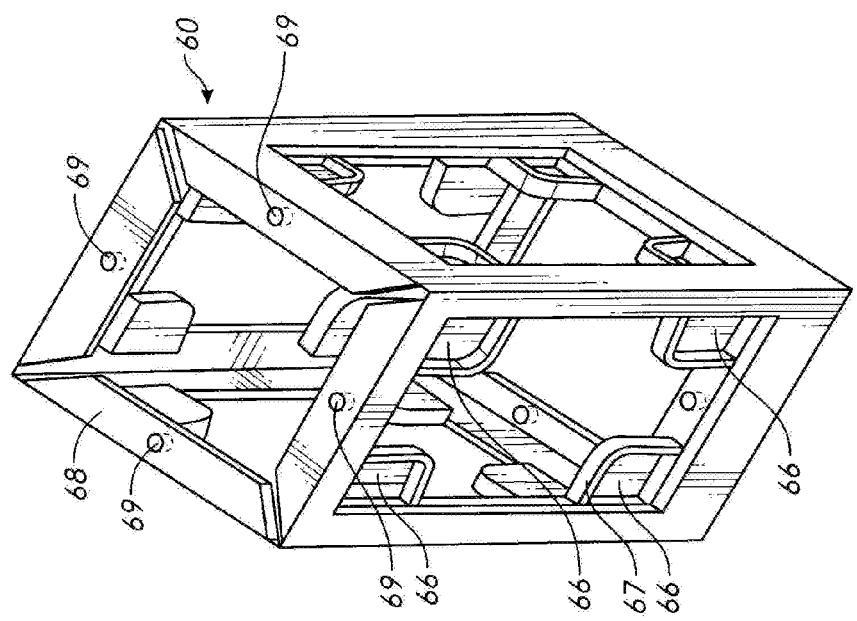
FIG. 10 is a perspective view of an exemplary frame used for the stereopter device shown in FIG. 9.

With reference to FIGS. 10-11, the second device embodiment differs from the first device embodiment in that the housing comprises a substantially rectangular cuboid shaped frame 60 on which the lateral side walls 58 are designed to couple or decouple by means of a quick-release connection. In the embodiment illustrated, the quick-release connection comprises four annular magnets 62 attached on the interior side 61 of the lateral side walls 58 by any suitable means (e.g., glue, epoxy, or the like), and cup-like recesses 66 made of a magnetic material coupled to the corners on each lateral face of the frame 60. The cup-like recesses may be attached to the frame 60 by any suitable means or formed as an integral portion of the frame. The lateral side 67 of the cup-like recesses 66 is preferably arcuate to match the curvature of the lateral surface of annular magnets 62 so as to facilitate alignment of the lateral side walls. Inward bevels 65 along the vertical edges of the lateral side walls 58 also facilitate alignment with adjacent lateral side walls. Tab-like overhangs 63 on the top and bottom of lateral side walls are provided to assist in uncoupling lateral side walls from the frame. The interior side of the tab-like overhangs may further comprise a label 64 indicating the proper response for the test set, for example "CF" (center-far).

Those of skill in the art will appreciate that other types of quick-release connections as defined in the present disclosure may be used to attach the lateral side walls 58 to the frame 60.

Accordingly, stereopter devices in accordance with the present disclosure which use an alternative or modified design of quick-release connection for attaching lateral side walls to a frame are considered within the scope of the present invention.

With reference to FIG. 11, design considerations for test sets 57 used with the second device embodiment are the same as for the first device embodiment. Test sets 57 may be attached on the interior side 61 of each lateral side wall 58 by any suitable means (e.g., glue, epoxy, screw, etc.).

Figure 12:
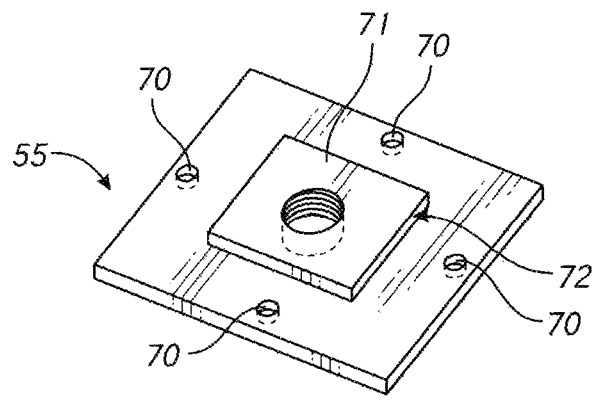
FIG. 12 is a perspective view of the interior side of end plate 55 of the stereopter device shown in FIG. 9.
Figure 13:
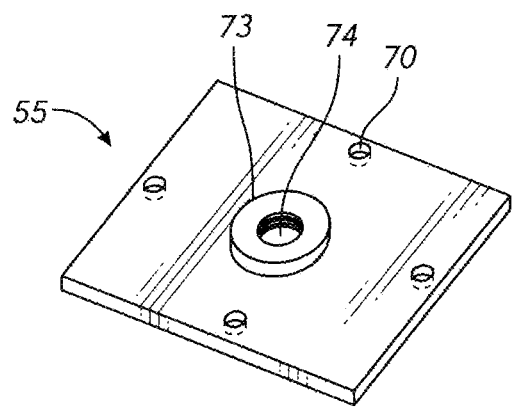
FIG. 13 is a perspective view of the exterior side of end plate 55 shown in FIG. 12.
Figure 14:
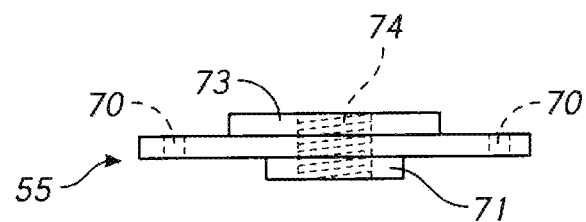
FIG. 14 is a side elevation view of end plate 55 shown in FIGS. 12-13.

Referring to FIGS. 12-14, end plates 55 for the second device embodiment are directly coupled to flanges 68 on the top and bottom of the frame 60 using screws (not shown) inserted through bore holes 70 on the end plates into threaded holes 69 on the frame (see FIG. 10). The interior surface of each end plate 55 preferably comprises a substantially rectangular reflecting element 71 having lateral surfaces 72 which are dimensioned so as to oppose the inner surface of a substantially rectangular diffuser similar to the diffuser used in the first device embodiment (see 8 in FIG. 4). Substantially centered on the exterior surface of each end plate 55 (see FIG. 13) is an annular flange 73 comprising a threaded bore hole 74 for attaching a handle 59. Handles similar in design to the handles used for the first device embodiment are suitable for use with the second device embodiment.

The dimensions of the second stereopter device embodiment and of its parts are similar to those of the first device embodiment. The frame 60, end plates 55, test sets 57, lateral side walls 58, and handles 59, may be made from any suitable material, but are preferably metal. Aside from the inner diffuser, all exterior surfaces, and any interior surfaces visible through test windows (including test objects), are preferably coated with a non-reflective dark material, for example, dull black paint.

The manner of using the second stereopter device embodiment for testing depth perception is the same as previously discussed for the first device embodiment. The second device embodiment, however, is especially useful where repeat testing of test subjects is contemplated. In particular, the orientation and initial arrangement of the lateral side walls (and thus the test sets) can be randomly selected by an examiner immediately prior or during each examination. The design of the second device embodiment also permits facile presentation of distinct sets of test sets which measure different binocular disparities.

A third stereopter device embodiment of the present disclosure (not shown) preferred for use with only a single quick release handle differs from the first device embodiment only in the design of the end plates and handle. FIG. 15 shows an end plate for the third stereopter embodiment having threaded cavities 75 which align with bore holes 10 for coupling to the lateral side walls 2 (see FIG. 4) using screws. The end plate also comprises on its interior side a substantially rectangular reflecting element 76 having lateral surfaces 77 which are dimensioned so as to oppose the inner surface 13 of the diffuser 8 (see FIG. 4).

Referring to FIGS. 15-16, the exterior surface of the end plate comprises a centrally positioned bore 78 having portions which define a larger diameter bore 82 defining the interior of an end plate annular collar 81 which passes partway through the bore 78, and a smaller diameter bore 83 which passes through to the interior side of the end plate and is concentric with the larger bore so as to define a step 84. The portion of bore 78 defining the smaller diameter bore 83 further comprises two slots 80 extending outward in opposite radial directions. Referring again to FIG. 15, the interior surface of the end plate comprises two positioning grooves 79 extending outwards in opposite radial directions from the portion of smaller bore diameter 83 and having widths substantially identical to that of the slots 80.

FIG. 17 shows the proximal end of a preferred quick release handle assembly which permits rapid coupling and decoupling to the end plate shown in FIGS. 15-16. The handle assembly 85 comprises a handle barrel 96 having a lamp 92 electrically connected through a simple single-pole switch 93 which is actuated by a switch button 94 to electrically connect and disconnect the lamp to a DC voltage source, such as that provided by one or more batteries 95. The switch and batteries are contained in the barrel 96 portion of the handle which further comprises a threaded proximal end 87 and an annular collar 86 having a diameter slightly smaller than the larger diameter bore 82 of the end plate. The handle assembly further comprises a compression spring 88 having an inner diameter larger than the diameter of the barrel 96, and an outer diameter smaller than the annular collar 86 of the barrel 96. Preferably spring 88 has closed and ground ends to permit maximal engagement with the annular collar 86. Referring to FIGS. 17-18, the handle assembly also comprises a cap 89 having an interior threaded cavity 90 for receiving threaded proximal end 87 of the handle barrel, a lamp bore hole 97, and two wing-like projections 91 extending radially in opposite directions from the cap on the proximal end.

FIG. 19 shows the fully assembled handle assembly. As seen in the figure, lamp 92 passes through lamp bore hole 97 (see FIG. 18) on the cap 89. Compression spring 88 is held in place in a partially compressed state 82 between collar 86 and wing-like projections 91 of the cap. Because the shape of the proximal end of the cap (see FIG. 18) is complementary to the shape formed by the smaller diameter bore 83 and slots 80 on the end plates (see FIG. 16), the wing-like projections 91 of cap 89 can pass entirely through bore 78 of the end plate. Spring 88, in contrast, cannot pass through the smaller diameter bore 83, but instead engages step 84 resulting in further compression. Accordingly, rotation of a fully inserted cap 89 allows the wing-like projections 91 to align with positioning grooves 80 on the interior of the end plate whereby partial relaxation of the spring 88 forces the wing-like projections 91 to engage grooves 80 and thus lock the handle assembly into place. FIG. 20 shows the handle assembly in the locked state following insertion into the end plate and rotation.

The manner of using the third stereopter device embodiment of the present disclosure for testing depth perception is similar to the procedure previously discussed for the first stereopter device embodiment. When only a single handle is used, during testing the examiner grips the handle (preferably positioned below the housing) in one hand and optionally grips the upper portion of the housing with the other hand in order to keep it steady during presentation of test sets to a test subject. Following presentation of test sets in the first orientation, the quick release handle can be decoupled from the end plate and attached to the other end plate, whereby the test sets are then presented in the opposite orientation.

It is to be understood that the above-described embodiments are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A device comprising:
   a housing having a top, bottom and at least one lateral surface;
   at least three real depth perception test sets coupled to said at least one lateral surface such that the planes defined by the vertical and horizontal axes of said test sets intersect to define the side surfaces of a right prism with a substantially convex regular polygonal base such that the positions of said test sets are substantially rotationally symmetrical with one another relative to a central axis, and wherein each said test set lacks rotational symmetry around a horizontal plane bisecting said test set;

at least three windows in said at least one lateral surface which are aligned with said test sets so as to permit viewing of said test sets;

a diffuser having planar faces rotationally symmetrical with one another relative to said central axis which are substantially aligned with and substantially parallel to said test sets, wherein said planar faces of the diffuser define an interior space within the housing which is interior to the test sets in relation to the central axis;

a first actuatable light source capable of illuminating said interior space; and a first elongated handle attached to said top or bottom surface of the housing, wherein the longitudinal axis of said first elongated handle is substantially aligned with said central axis such that rotation of said first elongated handle permits said test sets to be individually rotated into the field of vision of a stationary test subject.

2. The device of claim 1, wherein the number of lateral surfaces is identical to the number of said test sets.

3. The device of claim 2, wherein the lateral surfaces are substantially planar, and wherein each lateral surface is aligned with and parallel to the plane defined by the vertical and horizontal axes of a single test set.

4. The device of claim 3, wherein the number of test sets is between 3 and 8.

5. The device of claim 4, wherein the number of test sets is 4 or 6.

6. The device of claim 4, wherein said first actuatable light source comprises a first lamp electrically connected to a first switch and a first battery.

7. The device of claim 6, wherein said first actuatable light source is an integral part of said first elongated handle.

8. The device of claim 6, wherein said first elongated handle is a quick release handle capable of removable attachment to each of said top and bottom surfaces.

9. The device of claim 8, wherein said first actuatable light source is an integral part of said quick-release handle.

10. The device of claim 6, further comprising a second elongated handle attached to said housing opposite to said first elongated handle, wherein the longitudinal axis of said second elongated handle is substantially aligned with said central axis and said longitudinal axis of the first elongated handle.

11. The device of claim 10, wherein said first and second elongated handles are quick-release handles.

12. The device of claim 10, wherein said first actuatable light source is an integral part of said first elongated handle.

13. The device of claim 10, further comprising a second actuatable light source capable of illuminating said interior space, wherein said second actuatable light source comprises a second lamp electrically connected to a second switch and a second battery.

14. The device of claim 13, wherein said first actuatable light source is an integral part of said first elongated handle, and said second actuatable light source is an integral part of said second elongated handle.

15. The device of claim 14, wherein said first and second elongated handles are quick-release handles.

16. The device of claim 6, further comprising an internal frame and quick-release connections adapted for individual attachment and detachment of said lateral surfaces to said internal frame.

17. The device of claim 16, wherein said first actuatable light source is an integral part of said first elongated handle.

18. The device of claim 16, wherein said first elongated handle is a quick release handle capable of removable attachment to each of said top and bottom surfaces.

19. The device of claim 18, wherein said first actuatable light source is an integral part of said quick-release handle.

20. The device of claim 16, further comprising a second elongated handle attached to said housing opposite to said first elongated handle, wherein the longitudinal axis of said second elongated handle is substantially aligned with said central axis and said longitudinal axis of the first elongated handle.

* * * * *